United States Patent [19]

Yoshizumi et al.

[11] Patent Number: 4,565,698

[45] Date of Patent: Jan. 21, 1986

[54] MICROBIAL HAIR TONIC COMPOSITION

[75] Inventors: Hajime Yoshizumi, Takatsuki; Teruo Amachi, Takarazuka; Takaaki Kusumi, Suita; Takaharu Tanaka, Osaka; Hiroshi Ishigooka, Ibaraki, all of Japan

[73] Assignee: Suntory Limited, Osaka, Japan

[21] Appl. No.: 505,273

[22] Filed: Jun. 17, 1983

[30] Foreign Application Priority Data

Jun. 25, 1982 [JP] Japan ................................. 57-110395

[51] Int. Cl.$^4$ ...................... A61K 37/00; A61K 35/78
[52] U.S. Cl. .................................. 424/93; 424/195.1; 424/DIG. 4; 514/852
[58] Field of Search ............... 424/95, 93, 94, DIG. 4, 424/195.1; 514/852

[56] References Cited

PUBLICATIONS

Sewell et al., J. Chin. Micro. 16:236–239, 1982.

*Primary Examiner*—Albert T. Meyers
*Assistant Examiner*—John W. Rollins
*Attorney, Agent, or Firm*—Burns, Doane, Swecker & Mathis

[57] ABSTRACT

A microbial hair tonic composition containing, as an effective ingredient, cells belonging to species *Staphylococcus capitis*, or the crushed products, extracts, or cultured products thereof. This microbial hair tonic composition can effectively prevent the generation of dandruff and itching and can also effectively accelerate the growth of hair.

8 Claims, No Drawings

MICROBIAL HAIR TONIC COMPOSITION

BACKGROUND OF THE INVENTION

1. Field of the Invention

The present invention relates to a novel microbial hair tonic composition, suitable for use in maintaining the scalp and hair in normal condition. More specifically, it relates to a novel microbial hair tonic composition containing, as an effective component, cells belonging to species *Staphylococcus capitis*, or the crushed products, extracts, or the cultured products thereof, effective for preventing the generation of dandruff (or scurf) and itching in the hair and further for accelerating the growth of hair and preventing depilation (or falling-off of hair).

2. Description of the Prior Art

Various kinds of hair dressings or hair tonics in the form of, for example, lotions, hair oils, pomades (brilliantine), liquid brilliantines, hair creams, and set lotions are heretofore available on the market. These hair dressings mainly serve as an agent for affording a fresh feel to the scalp, for dressing hairs, or depressing the damage of hairs. So-called conventional hair-growers or hair-restores for accelerating the growth of hairs are those which prevent or depress depilation, especially falling-off of hair in the vertex portion by female hormones (e.g., estrogens), or those which stimulate hair bulbs by peripheral nervous stimulators such as Capsicum tincture (capsaicin), Cantharis tincture (cantaridin), Thujae tincture (hinokithiol), and Jaborandi tincture (pilocarpin). However, the effects of these conventional hair-growers are scientifically questioned from the standpoint of true hair growth acceleration.

SUMMARY OF THE INVENTION

Accordingly, an object of the present invention is to provide a novel microbial hair tonic composition containing, as an effective component, a microorganism which is capable of effectively preventing and eliminating the generation of dandruff and itching in the hair and also of exhibiting remarkable effects on the true acceleration of the growth of hair.

Other objects and advantages of the present invention will be apparent from the description set forth hereinbelow.

In accordance with the present invention, there is provided a microbial hair tonic composition containing, as an effective ingredient, cells belonging to species *Staphylococcus capitis*, or the crushed products, extracts, or cultured products thereof.

DESCRIPTION OF THE PREFERRED EMBODIMENTS

Good and profuse hairs throughout the life are common dream for human beings. Generation of dandruff and itching in hairs and depilation already occur from the younger generation to cause thin hair and premature baldness.

The inventors have found that *Staphylococcus capitis* constitutes all or most parts of a microflora in the scalp of those having healthy hair, after studying in detail the microflora of the above-mentioned scalp. Contrary to this, no substantial amount of *Staphylococcus capitis* is found in microflora and bacteria such as *Staphylococcus epidermidis* and *Corynebacterium acnes* are present as a main microflora phase, instead of *Staphylococcus capitis*, in the scalp of those having unhealthy hair and scalp such as the generation of dandruff and itching in the scalp and abnormal depilation. This means that the transition of the microflora in the scalp from *Staphylococcus capitis* to bacteria such as *Staphylococcus epidermidis* and *Corynebaceterium acnes* is an indication of the generation of, for example, dandruff and itching, and abnormal depilation. As a result, the inventors have found that abnormal conditions of hair such as the generation of dandruff itching, and abnormal depilation can be prevented and/or repressed by dropwise applying a dispersion of *Staphylococcus capitis* to the scalp in the above-mentioned abnormal conditions. Furthermore, this improved effect can be obtained by the use of the crushed products, extracts, and cultured products of the cells of *Staphylococcus capitis*.

The cells of *Staphylococcus capitis*, and the crushed products, extracts, and cultured products thereof can be included, as an effective component, in a hair tonic, together with the other conventional effective components and auxiliary additives as mentioned hereinbelow.

According to the present invention, *Staphylococcus capitis* can be equally used for the purpose of the present invention in the form of natural cells or artificial mutant cells, or the crushed products, extracts, or cultured products thereof ("SC cells" hereinbelow). However, the use of the dried live cells of *Staphylococcus capitis* obtained by freeze drying or other means can be practically advantageously used from the viewpoint of easy handling.

When the SC cells are applied to the scalp and hair in the above-mentioned abnormal conditions for a relatively long period, the propagation of microorganisms harmful to human hair is depressed and the microflora is changed to a normal flora mainly containing *Staphylococcus capitis*. As a result, abnormal conditions such as the generation of dandruff and itching in the hair and the scalp and the depilation are effectively improved according to the present invention.

*Staphylococcus capitis* contained as a main effective ingredient in the microbial hair tonic according to the present invention is a known microorganism which is, for example, freely available from ATCC (American Type Culture Collection, Rockville, Md, U.S.A.) as ATCC-27840 to ATCC-27843 as listed in the brochure published in 1982 from ATCC.

Furthermore, the cells of *Staphylococcus capitis* can be isolated from the scalps in healthy conditions as follows:

A sterilized cotton swab stick is wetted with a 0.075M phosphate buffer solution (pH 7.9) containing 0.1% of Tween 80 (polyoxyethylene-sorbitan fatty acid ester type nonionic surfactant available from Atlas Powder Co.) and, then, the scalp is rubbed with the wetted cotton swab. The cotton swab is then rubbed on the surface of a P-agar culture medium containing 10 g of peptone, 1.5 g of yeast extract, 5 g of sodium chloride, 1 g of glucose and 15 g of agar in 1000 ml of water and, then, the P-agar culture medium is cultured at a temperature of 37° C. for 48 hours. Thus, colonies of *Staphylococcus capitis* and small amounts of other bacteria are grown. The SC cells are recovered from these colonies by means of a micromanipulator or platinum wire. The SC cells thus recovered are again inoculated into another P-agar medium and isolated. This operation can be repeated two or more times as required. Thus, pure cultured SC cells can be obtained.

The morphological characteristics of the strain belonging to the SC bacterium isolated according to the above-mentioned procedure as shown below. This bacterium is not described in the standard bacteria classification text, "Bergy's Manual of Determinative Bacteriology (8th edition, 1974)". The identification of the bacterium was carried out according to the descriptions in W. E. Kloos et al. "Int. J. Syst. Bacteriol., Vol. 25, No. 1, 50–79 (1975)".

(A) Morphological characteristics
  (1) Shape and size of cell: spheres having a diameter of 0.8 to 1.2 μm, present in agglomerates containing 2 to 4 cells
  (2) Motility: none
  (3) Sporulation: not observed
  (4) Gram stain: positive
  (5) Acid resistance: none (B) States of growth
  (1) Meat extract-agar plate culture: moderately raised, circular, smooth surface, opaque white small colony having a size of 1 to 3 mm is formed.
  (2) Meat extract-liquid culture: good growth, turbid in entire liquid
  (3) Meat extract-gelatin stab culture: no liquefaction of gelatin, filamentous growth
  (4) Meat extract-agar slant culture: good growth, moderately raised, smooth surface, opague, white
  (5) Litmus milk: no change in color, no solidification, no liquefaction
  (6) Methyl red (MR) test: positive
  (7) Voges-Proskauer (VP) test: positive
  (8) Production of indole: none
  (9) Production of hydrogen sulfide: none
  (10) Hydrolysis of starch: none
  (11) Utilization of citric acid: positive in Koser's citrate and Christensen's citrate medium
  (12) Utilization of inorganic nitrogen source: utilize nitrates but not utilize ammonium salts
  (13) Production of pigments: none
  (14) Urease test: negative
  (15) Oxidase test: negative
  (16) Catalase test: positive
  (17) Range of conditions of growth:
    (i) pH for growth 5 to 9
    (ii) Temperature for growth 20° C. to 40° C.
    (iii) Optimum growth temperature 32° C. to 35° C.
  (18) Oxygen relation: anaerobic
  (19) Utilization of sugars:
    (i) Acid production: positive D-glucose, D-fructose, D-mannose, sucrose, glycerol
    (ii) Acid, gas production: negative D-galactose, D-xylose, L-arabinose, maltose, lactose, trehalose, D-sorbitol, inositol, starch
    (iii) Lactic acid is produced from D-glucose.
  (20) Sodium chloride resistance: positive (good growth in 10% to 20% aqueous sodium chloride solution)
  (21) Lipase activity: positive
  (22) Lecithinase activity: positive
  (23) Coagulase activity: negative
  (24) Phosphatase activity: negative
  (25) Deoxyribonuclease: positive Various theories have been proposed relating to the causes of depilation, epilation, dandruff, and itching. For example, an unbalanced hormone constitution theory, a nutrient relating theory, a seborrhea theory, and a genetic or hereditary theory are known. Anyway, it appears that there will be a high correlation between the above-mentioned abnormal conditions and the development of glandula sebacea (Masumi Inaba, "Mainichi Life" November, 1981, pages 26 to 35; "Saishin Keshohin Kagaku) Recent Cosmetics Science)", page 130 published by Yakuji Nippo Sha in 1980).

According to Inaba, when the glandula sebacea of a head portion is developed by nutrients, hormones or the like, testosteron is converted to stronger 5 alpha-dihydrotestosteron ("5α-DHT" hereinbelow) by 5α-reductase present in the glandula sebacea. This transfers to hair papilla via blood vessels to thereby depress the activities of adenylcyclase in hair-matrix cells. As a result, it is believed that hair-follicles gradually become small to cause involution and, therefore, hair becomes thin and downy to cause a bald head.

On the other hand, dandruff is formed by the fact that selium secreted and exudated to the surface of scalp in a large amount due to the hypertrophy of glandula sebacea is mixed with horney or keratin peeled off from the surface of scalp. The dandruff thus formed inhibits dermal or skin respiration and the intake of nutrients into the fibril (or hair-root) portions. This also causes a bald head.

It has been found that the SC cells used as a main ingredient in the present invention have both lipase activity and 5α-reductase inhibition activity. Accordingly, the microbial hair tonic composition according to the present invention can decompose sebum to remove dandruff and itching due to the lipase function of the SC cells and can depress the production of 5α-DHT due to the 5α-reductase inhibition function of the SC cells. Furthermore, the growth of glandula sebacea is depressed and a division capability of hair-matrix cells is increased by the synergetic effect of the lipase function and the 5α-reductase inhibition activity of the SC cells. As a result, depilation and epilation are effectively prevented and the growth of hairs is effectively accelerated.

The microbial hair tonic compositions according to the present invention can be embodied as follows:

(1) A $10^6$ to $10^8$ cell/ml amount of the pure-cultured living SC cells is suspended in a distilled water or a 0.01% to 0.1% typically 0.1% aqueous surfactant solution. This can be directly applied to the human head, or can be incorporated into any cosmetic compositions for human, especially men's hair.

(2) The SC cells obtained from pure culture are dried by means of, for example, freeze-drying or vacuum drying under aeration to form the dried cells. These dried cells can be applied to the human head after suspending the same in water or an aqueous surfactant solution having the above-mentioned surfactant content. For example, the vacuum or freeze dried SC cells supported on an adsorbing material such as a filter paper or a cotton swab and water or an aqueous surfactant solution for suspending the SC cells are separately enclosed in sealed vessels to form a kit for mixing upon use.

(3) Furthermore, the SC cells obtained from a pure culture, or the crushed products or extracts thereof are dispersed in a concentration of, for example, 0.01% to 1.0%, in a base liquid such as propylene glycol, liquid paraffin, ceresin, and Vaseline, petroleum jelly to thereby form in the form of, for example, hair rinse, hair oil, pomade, hair cream, or set lotion.

It should be noted that the above-mentioned embodiments are only illustrative and that various variations and modifications can be effected within the spirit and scope of the present invention. In addition to the above-mentioned ingredients, various conventional ingredients suitably used in the formulation of a hair tonic composition or a hair dressing composition can be incorporated in a conventional amount into the microbial hair tonic composition. Typical examples of such ingredients are cantharis tincture, Jaborandi tincture, follicle hormones, vitamin E, vitamin E nicotinate, pantothenic acid, resorcinol monoacetate, beeswax, etyl alcohol, triethanolamine, borax, lower alcohol esters of $C_{14}$ to $C_{18}$ saturated fatty acids, glyceryl monostearate, glycerol, isopropyl myristate, stearic acid, castor oil, citric acid, organic acids, plant gums, and perfumes.

Especially since a lotion is applied to the hair directly after hair washing and is deposited on the scalp and hair, a lotion containing the SC cells, or the crushed products or extract thereof, is a desirable embodiment of the present invention. Furthermore, the incorporation of the SC cells, or the crushed products or extract thereof into a hair cream is also a practical embodiment of the present invention, since a hair cream is commonly used for hair dressing.

The microbial hair tonic composition of the present invention can be applied to the scalp and hair after hair washing or at hair dressing in any of the above-mentioned formulation forms. The application is desirably effected in an amount of $10^6$ to $10^8$ cell/time and 1 to 3 times a day. For example, an aqueous suspension containing about $10^7$ cell/ml can be desirably applied (i.e., coated or spread) to the scalp in an amount of about 3 ml each time.

The nonpathogenicity of Staphylococcus capitis is confirmed as reported in C. M. Sewell et al. "J. Clin. Microbiol. Vol. 16, No. 2, 236–239 (1982)" and D. J. Smith et. al. "Eur. J. Clin. Microbiol., No. 4, 228–232 (1982)." The inventors have also confirmed that no abnormal condition was observed when 2 ml each of a suspension of $10^8$ cells/ml of the SC cells in distilled water was spread on the scalp 2 times per day for 5 months.

EXAMPLES

The present invention will now be further illustrated by, but is by no means limited to, the following Examples.

Example 1: Microflora on men's head

As mentioned hereinabove, the inventors found that the microflora in the scalp of having healthy hair mostly or mainly constituted Staphylococcus capitis, and only 1% to 4% other bacteria such as Staphylococcus epidermidis and Staphylococcus aureus, based on the number of the total bacteria in the microflora. Contrary to this, only an extremely small percentage (sometimes substantially zero) of Staphylococcus capitis was present in the microflora in the scalp of those having unhealthy hair and, instead, 30% to 50% or more of Staphylococcus epidermidis was present.

The experimental results are shown in Table 1 below.

TABLE 1

| | | Distribution of Microorganisms in Scalp | | | Condition of scalp and hair | | |
|---|---|---|---|---|---|---|---|
| Subject | Age | St. capitis | St. epidermidis | Other Microorganisms | Amount of hair*[1] | Dandruff*[2] | Itching*[2] |
| A | 36 | 97.9% | 2.1% | — | +++ | — | — |
| B | 32 | 100.0 | 0 | — | +++ | — | — |
| C | 26 | 99.84 | 0.14 | Bacillus brevis 0.01%, Serratia marcescens 0.01% | +++ | + | + |
| D | 42 | 86.4 | 13.1 | Corynebacterium Sp. 0.5%, Acinetobacter calcoaceticus ± | ++ | + | ++ |
| E | 34 | 82.4 | 16.9 | Micrococcus luteus 0.5%, Fungi + Yeast 0.2% | ++ | — | — |
| F | 26 | 16.8 | 80.7 | Corynebacterium sp. 2.5% | +++ | ++ | — |
| G | 39 | 62.0 | 37.9 | Corynebacterium sp. 0.1% | ++ | + | + |
| H | 31 | 89.6 | 7.5 | Micrococcus luteus, roseus 1.5%, Corynebacterium sp. 0.8%, yeast 0.5% | +++ | + | — |
| I | 40 | 0.5 | 99.5 | — | + | — | — |
| J | 28 | 89.3 | 10.7 | — | ++ | — | + |

*[1]: +++ Thick hair, ++ Somewhat thin hair, + Thin hair, partially bald-patch
*[2]: ++ Remarkably large, + Somewhat positive, — Negative As is clear from the results shown in Table 1, 95% or more of the microorganisms present in men's scalp is Staphylococcus capitis and Staphylococcus epidermidis. Furthermore, 90% or more of the microorganisms present in men's scalp having good hair and scalp conditions is Staphylococcus capitis. Accordingly, it is believed that Staphylococcus capitis is present in human scalp to maintain the hair in normal or good conditions. If the balanced condition between Staphylococcus capitis and the other microorganisms in the scalp is lost for certain reasons, the hair conditions are transferred from good conditions to abnormal conditions with decrease in the amount of Staphylococcus capitis present in the microflora of the scalp.

Example 2: Lipase Activity of Staphylococcus capitis

Lipase activity of SC cells were determined as follows:

SC cells were cultured at a temperature of 28° C. for 48 hours in a P-liquid medium containing 1.0% (V/V) of olive oil and the cultured product was centrifugally separated. The lipase activities of the cultured filtrate and the cultured cells were measured by titrating the amount of the free fatty acid formed in the presence of olive oil as a substrate with an 1/20M aqueous potassium hydroxide solution. The composition of the reaction mixture was 9 ml of a phosphate buffer solution (1/20M, pH=6.9), 1 ml of an aqueous calcium chloride solution (1/10M), 1 g of a substrate (olive oil, Tween 20 available from Kao Atlas Co., or lecithin), and 1 ml of the cultured filtrate or the crushed cell solution (wet weight of the cell segments=100 mg/ml). The reaction was carried out at a temperature of 30° C. for 24 hours while shaking.

The results are shown in Table 2.

TABLE 2

| | Free fatty acid μmole/24 hours | |
|---|---|---|
| Substrate | Cultured filtrate | Crushed cell solution* |
| Olive oil | 75 | 420 |
| Tween 20 | 28 | 55 |

TABLE 2-continued

| | Free fatty acid μmole/24 hours | |
|---|---|---|
| Substrate | Cultured filtrate | Crushed cell solution* |
| Lecithin | 265 | 163 |

*Wet weight of the cell segments = 100 mg/ml

As is clear from the above results, the SC cells have lipase activity against various fatty acid containing substrates.

Example 3: 5α-Reductase Inhibition Activity of *Staphylococcus capitis*

Prostrate gland cells of rats were crushed and, then, a specimen of testosterone 5α-reductase was prepared by separating microsome from the crushed liquid mixture. The conversion of the testosterone to 5α-DHT by the use of the above-prepared enzyme specimen was monitored by radioisotopically labelled testosterone. After the completion of the reaction, the reaction mixture was extracted with ethyl acetate and the extract was double developed by silica gel thin layer chromatography (solvent system, dichloromethane:cyclohexane:acetone=15:4:1). The amounts of testosterone and 5α-DHT were determined from the intensities of the radioactivity.

Preparation of Reaction Mixture

A 5 μl amount of a reduced form of NADP (nicotinamide adenine dinucleotide phosphate) ($10^{-1}$M) and 5 μl of a mixture of glucose-6-phosphate ($5\times10^{-1}$M) and glucose-6-phosphate dehydrogenase (0.2 unit) were added to 0.2 ml of a 0.05M aqueous $KH_2PO_4$ buffer solution containing 0.1% of BSA (bovine serum albumin) (pH=6.6). Then, a 0.1 ml fraction of the microsome obtained from the prostate gland cells of rats (containing 1.4 mg protein) and 0.1 ml of the crushed liquid product of the SC cells (the crushed product of *Staphylococcus epidermidis* cells and a phosphate buffer solution in the same amounts as controls) were added to the above-prepared mixture. Thus, the reaction mixtures were prepared.

Reaction

A $2.5\times10^{-3}$ μmol amount of testosterone and $3.4\times10^{-3}$ μmol of labelled testosterone were added to the above-prepared reaction mixture at a temperature of 25° C. such that the total amount of the reaction mixture became 0.5 ml and, then, the reaction mixture was allowed to be reacted for 40 minutes.

After the completion of the reaction, the reaction mixture was extracted with ethyl acetate by adding 0.5 ml of ethyl acetate to the reaction mixture. The extract was developed in the same manner as mentioned above and the intensity of the radioisotope was measured by using a scintillation counter.

The results are shown in Table 3.

TABLE 3

| Sample | Testosterone (A) cpm | 5α-DHT (B) cpm | $\frac{B}{A+B} \times 100\%$ |
|---|---|---|---|
| Phosphate buffer* | 4452 | 217 | 4.85 |
| Crushed product of *St. epidermidis* cells* | 5144 | 214 | 3.99 |
| Crushed product of SC cells | 5084 | 50 | 0.97 |

*Control

As is clear from the results shown in Table 3, the conversion ratio of testosterone to 5α-DHT by the crushed product of the SC cells according to the present invention is only one-fourth or less of those of the controls. Thus, it is clearly observed that the crushed product of the SC cells has a strong 5α-reductase inhibition activity.

Example 4: Production of Freeze Dried SC Cell

SC cells available from ATCC (American Type Culture Collection) as ATCC 27840 were subjected to pure culture as follows: That is, SC cells were inoculated into 500 ml of flasks containing 200 ml of P-medium and were grown in a shaking incubator at 30° C. for 1 day.

The cultured SC cells were centrifugally separated at 7000 G for 20 minutes and, then, the separated cultured cells were washed several times with a 1/50M phosphate solution having a pH of 6.9. The washed cultured cells were freezed dried as follows: That is, the cells were resuspended with distilled water and were rapidly frozen by using ethanol-dryice. The frozen cells were dried in vacuo. Thus, freeze dried SC cells were obtained.

Example 5: Production of Lotion Type Microbial Hair Tonic Composition

A 100 mg amount of the freeze dried SC cells obtained in Example 4 above was dispersed in 5 ml of purified water containing 0.1% of Tween 20 dissolved therein. Thus, a lotion type microbial hair tonic composition containing the SC cells was formulated.

Example 6: Production of Hair Cream Composition

A hair cream composition having the following compositions were formulated:

| | |
|---|---|
| Liquid paraffin | 50% |
| Polyethylene glycol | 1% |
| Tween 20 | 1% |
| Freeze dried SC cells obtained in Example 4 | 5% |
| Purified water | 43% |

Example 7: Production of Aerosol Type Microbial Hair Tonic Composition

An aerosol type microbial hair tonic composition was prepared as follows:

A 10 mg amount of the freeze dried SC cells obtained in Example 4 was added to 5 ml of purified water containing 1% of polyoxyethylene lanolin, 2.5% of lanolin alcohol, 0.5% of glycerol fatty acid ester 1 and 0.2% of perfume. Then, the mixture was charged into a vessel and, after sealing the vessel, nitrogen gas was pressurized into the vessel.

Example 8: Application of Lotion Type Microbial Hair Tonic Composition

The lotion type microbial hair tonic composition prepared in Example 5 was applied, twice a day, to the scalp of 20 men at ages of 28 to 40 in an amount of 3 ml each for 6 months. The subjects selected were ten members having a large amount of dandruff and ten members having a large amount of depilation.

The results are shown in Table 4.

TABLE 4

| Condition | Effect | | |
| --- | --- | --- | --- |
| | Excellent | Good | None |
| Dandruff | 9 | 1 | 0 |
| Depilation | 6 | 2 | 2 |

We claim:

1. A microbial hair treatment composition comprising $10^6$ to $10^8$ cells/ml of cultured living *Staphylococcus capitis* and a suitable solvent.

2. The microbial hair treatment composition according to claim 1 further comprising 0.01–0.1% by weight of a nonionic surfactant.

3. The microbial hair treatment composition according to claim 1 wherein said solvent is distilled water.

4. The microbial hair treatment composition according to claim 1 wherein said cultured living *Staphylococcus capitis* cells are dispersed in propylene glycol, liquid paraffin, ceresin, or petroleum jelly.

5. A microbial hair treatment composition comprising $10^6$ to $10^8$ cells/ml of freeze dried live cells of *Staphylococcus capitis* and a suitable solvent.

6. A microbial hair treatment composition according to claim 5 further comprising 0.01–0.1% by weight of a nonionic surfactant.

7. The microbial hair treatment composition according to claim 5 wherein said solvent is water.

8. A microbial hair treatment composition comprising 0.01–1.0% by weight of crushed products of *Staphylococcus capitis* in a propylene glycol, liquid paraffin, ceresin, or petroleum jelly base liquid.

* * * * *